United States Patent [19]

Sondergeld et al.

[11] Patent Number: 4,912,979
[45] Date of Patent: Apr. 3, 1990

[54] METHOD AND APPARATUS FOR DETECTING AND MEASURING ELASTIC ANISOTROPY

[75] Inventors: Carl H. Sondergeld, Broken Arrow; Chandra S. Rai, Tulsa; Richard M. Alford, Broken Arrow, all of Okla.

[73] Assignee: Amoco Corporation, Chicago, Ill.

[21] Appl. No.: 310,485

[22] Filed: Feb. 14, 1989

Related U.S. Application Data

[63] Continuation of Ser. No. 108,847, Oct. 14, 1987, abandoned.

[51] Int. Cl.$^4$ ............................................. G01N 29/00
[52] U.S. Cl. ......................................... 73/594; 367/35
[58] Field of Search ................. 73/594, 599; 367/35, 367/73

[56] References Cited

U.S. PATENT DOCUMENTS

| | | | |
|---|---|---|---|
| 4,631,963 | 12/1986 | Sprunt et al. | 73/594 |
| 4,631,964 | 12/1986 | Sprunt et al. | 73/594 |
| 4,641,520 | 2/1987 | Mao | 73/151 |
| 4,713,968 | 12/1987 | Yale | 73/594 |
| 4,789,969 | 12/1988 | Naville | 367/36 |

FOREIGN PATENT DOCUMENTS 0169075 1/1986 European Pat. Off. .
0169076 1/1986 European Pat. Off. .

OTHER PUBLICATIONS

Yariv, A., "Optical Electronics 3rd Ed." 1985, pp. 10-11.

Primary Examiner—John Chapman
Assistant Examiner—Lawrence Fess
Attorney, Agent, or Firm—Timothy D. Stanley

[57] ABSTRACT

A novel method for detecting and measuring elastic anisotropy in a sample of the earth's formations is provided. A dyad of time series signal representative of the sample's response to imparted shear waves is recorded. The dyad of time series signals can then be processed to detect and measure elastic anisotropy in the sample. More particularly, the dyad of time series signals are collected by imparting shear waves having first and second polarizations into the samples with a shear wave transducer and recording the sample's response to each of the imparted shear waves by shear wave transducers having first and second polarizations. In one embodiment of the invention, the dyad of time series signals can be diagonalized to detect and measure elastic anisotropy in the sample. In another embodiment, the dyad of time series signals can be processed for a plurality of rotation angles and the resulting rotated dyad of time series signals can be displayed to detect and measure elastic anisotropy in the sample.

29 Claims, 10 Drawing Sheets

INPUT        $\varphi_{12}$        $\varphi_{21}$

METHOD AND APPARATUS FOR DETECTING AND MEASURING ELASTIC ANISOTROPY

This is a continuation of copending application Ser. No. 108,847, filed on Oct. 14, 1987, now abandoned.

BACKGROUND OF THE INVENTION

The present invention relates generally to a method and apparatus for detecting and measuring elastic anisotropy in samples of the earth's formations.

It has generally been acknowledged that single crystal materials can exhibit elastic anisotropy which is related to their crystallographic symmetry. Since rocks are generally an aggregate assembly of minerals, which was assumed to be random, such rocks have generally been assumed to be isotropic. If, however, the mineral orientation is not random, one would then expect crystal-like anisotropy to be manifested in the rock properties. Rocks with pronounced visual fabrics such as shale, schists, and other metamorphic rocks as well as igneous rocks such as dunite have been clearly documented as possessing elastic anisotropy which is strongly related to their visual fabric and mineral composition. There exists other more subtle factors which can also give rise to anisotropic behavior such as the presence and orientation of cracks in the rock.

Generally, anisotropy has been a complication to be ignored by explorationists except in dealing with igneous and metamorphic rocks with a pronounced mineral alignment. However, it has become evident that sedimentary rocks as well as rocks containing fractures can have pronounced and measurable elastic anisotropy. In fact, recent seismic investigations have indicated that the greater portion of the earth's crustal surface may be more anisotropic than originally believed. Consequently, previous laboratory measurements of acoustic velocities of samples from sedimentary basins, which can depend upon the presence or absence of anisotropy, are generally believed to have been in error since anisotropy, as a matter of principle, has not been taken into account. Laboratory studies concerning formation anisotropy have generally focused upon velocity analysis and have paid little attention on the amplitude dependence of anisotropy. More recently Sprunt, et al., in U.S. Pat. Nos. 4,631,963 and 4,631,964 described a method and apparatus for measuring shear wave velocity anisotropy in formation samples.

The present invention provides a novel method for accurately determining elastic anisotropy both in terms of magnitude and symmetry in formation samples which greatly simplifies and expedites the detection and measurement of such elastic anisotropy.

SUMMARY OF THE INVENTION

A novel method and apparatus for detecting and measuring elastic anisotropy in samples of the earth's formations is provided. A dyad of time series signals representative of a sample's response to imparted shear waves is recorded. The dyad of time series signals can then be processed to detect and measure elastic anisotropy in the sample. More particularly, the dyad of time series signals are collected by imparting shear waves having first and second polarizations. The sample's response to each of the imparted shear waves is recorded by shear wave transducers having first and second polarizations. In one embodiment of the invention, the dyad of time series signals can be diagonalized to detect and measure elastic anisotropy in the sample. In another embodiment, the dyad of time series signals can be processed for a plurality of rotation angles and the resulting rotated dyad of time series signals can be displayed for selected rotation angles to detect and measure elastic anisotropy in the sample.

The present invention provides a novel apparatus for recording a dyad of time series signals representative of the response of a sample of the earth's formations to imparted shear waves to detect and measure elastic anisotropy in the sample. The apparatus also includes processing means for processing the dyad of time series signals to detect and measure elastic anisotropy in samples of the earth's formations. By recording a dyad of time series signals, the detection and measurement of elastic anisotropy in samples of the earth's formation is greatly simplified and expedited. In one embodiment of the apparatus, first and second shear wave transmitting transducers having orthogonal polarizations impart shear waves along a longitudinal axis of the sample. First and second shear wave receiving transducers having orthogonal polarizations record time series signals representative of the sample's response to each of the imparted shear waves at the opposite end of the sample. In another embodiment of the apparatus, a shear wave transducer rotatable between a first polarization and second polarization imparts shear waves along a longitudinal axis of the sample and a shear wave receiving transducer rotatable between a first polarization and a second polarization records the sample's response to shear waves imparted along the first and second polarizations.

DESCRIPTION OF FIGURES

FIG. 10b is a representation of a plurality of cross-component time series signals $\phi_{12}$ generated for a plurality of rotation angles for the McNabb shale of FIG. 10a.

FIG. 10c is a representation of a plurality of cross-component time series signals $\phi_{21}$ generated for a plurality of rotation angles for the McNabb shale of FIG. 10a.

DETAILED DESCRIPTION OF THE PREFERRED EMBODIMENTS

The present invention provides an apparatus and method for detecting and measuring elastic anisotropy in samples of earth formations.

Figure 1A:
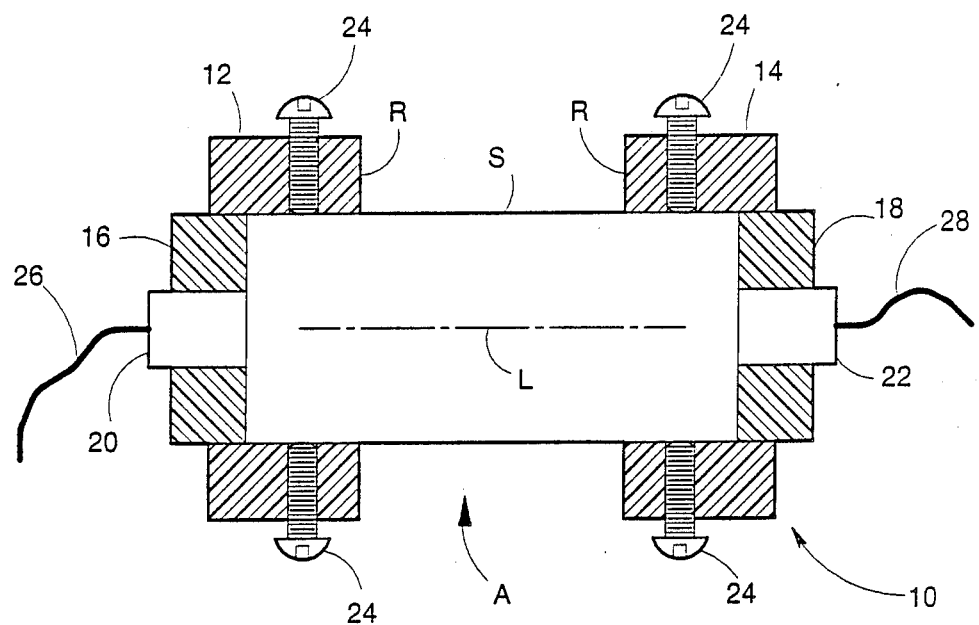
FIG. 1a is a cross-sectional representation of an apparatus for detecting and measuring elastic anisotropy in formation samples.
Figure 1B:
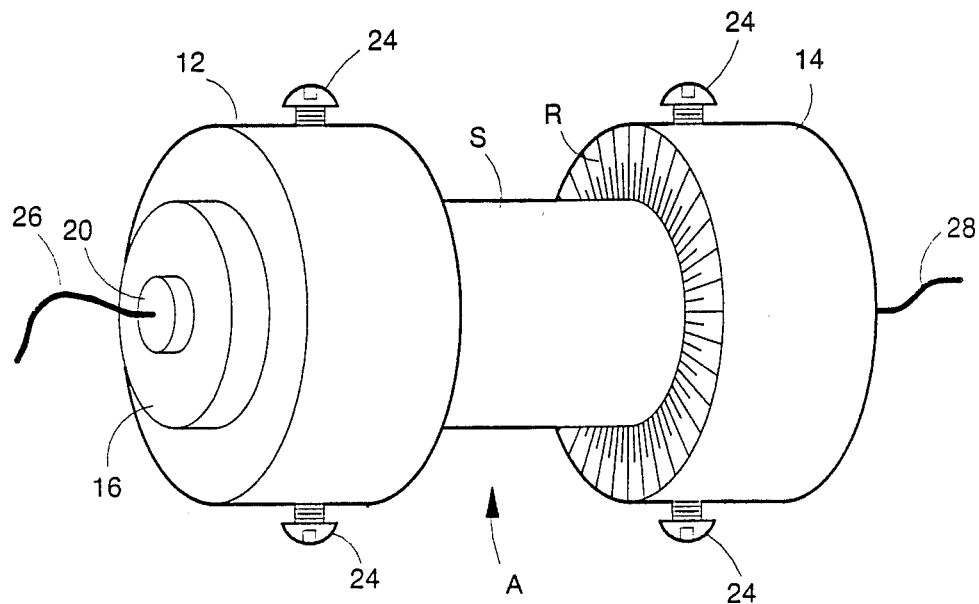
FIG. 1b is a perspective view of the apparatus of FIG. 1a for detecting and measuring elastic anisotropy in samples of the earth's formations.

With reference to FIGS. 1a and 1b, a test apparatus for detecting and measuring elastic anisotropy in formation samples has been developed. FIG. 1a provides a cross-sectional view of the test apparatus of the present invention and FIG. 1b provides a perspective view of the test apparatus of the present invention. The test apparatus is adapted to detect and measure the magnitude and symmetry effects of elastic anisotropy on both the velocity and amplitude of propagating shear waves in a sample S. The test apparatus includes a sample holder A comprising a pair of annuli 12, 14, each sized to receive the sample S. Each annulus 12, 14 further includes a buffer rod 16, 18 securely mounted thereto. Preferably, the buffer rods 16, 18 are made from isotropic materials (such as plexiglas) which have an impedance closely matching that of the sample to be evaluated. The annuli 12, 14 each include angular reference marks R. In a first embodiment of the test apparatus, each buffer rod 16, 18 has one shear wave transducer having a single polarization 20, 22 epoxied thereto. In a second embodiment of the test apparatus, the shear wave transducers 20, 22 each include two orthogonally polarized shear wave transducers. Hereafter, transducer 20 will be referred to as the transmitting transducer 20 and transducer 22 will be referred to as the receiving transducer 22. This distinction is made to simplify the following discussions since those skilled in the art will appreciate that either transducer 20 or 22 can be effectively employed as either a transmitting or receiving transducer.

The angular reference marks R associated with the annulus 12 can be used to orient the polarization of the transmitting transducer 20 with respect to a fixed reference (e.g., a fixed mark on the sample S) or with respect to the polarization of the receiving transducer 22. Similarly, the angular reference marks R associated with annulus 14 can be used to orient the polarization of the receiving transducer 22 with respect to a fixed reference mark (e.g., a fixed mark on the sample S) or with respect to the polarization of the transmitting transducer 20. Both annuli 12, 14 include a plurality of threaded fasteners 24 for fixing the azimuthal orientation of each plexiglas annuli 12, 14 (and hence the polarizations of the transmitting transducer 20 and the receiving transducer 22) with the longitudinal axis L of the sample S. The fasteners 24 also provide for rotary positioning of the polarized shear wave transducers 20, 22 at a plurality of azimuthal orientations with respect to the longitudinal axis L of the sample S. To ensure sufficient acoustic coupling of the shear wave transducers 20, 22 to the sample S, a viscous polymer (such as polystyrene) can be used to couple acoustic energy into and out of the sample S.

When a time-varying voltage of the test apparatus is applied to the transmitting transducer 20 (in the form of a single sine wave pulse of fixed amplitude and frequency) with input means 26, a shear wave can be imparted into the sample S and recorded by the receiving transducer 22 as a time series signal. The time series signal can be transmitted by output means 28 and subsequently amplified and digitized for further processing by a processing unit (not shown) to detect and measure elastic anisotropy in sample S as shall be discussed below.

Two separate angular indexing schemes can be employed in conjunction with the detection and measurement of elastic anisotropy. The first comprises the azimuthal angles $\psi_t$ and $\psi_r$ which can be measured in a relative sense either clockwise or counterclockwise from a fixed mark on sample S. The azimuthal angles $\psi_t$ and $\psi_r$ can be measured employing the angular reference marks R on the annuli 18, 20. Hence, the azimuthal angles $\psi_t$ and $\psi_r$ orient respectively the polarizations of both the transmitting transducer 20 and the receiving transducer 22 to a fixed direction on the sample S or to each other. Similarly, a second angle $\theta$ can be measured in a relative sense either clockwise or counterclockwise from a fixed mark on a sample S. The second angle $\theta$ is the angle measured between a principal elastic axis $\theta_p$ or the visual rock fabric $\theta_f$ of the sample S measured from a fixed reference mark on the sample S. Hence, the angle $\theta$ orients both the principal elastic axis and visual rock fabric of the sample S to a fixed azimuthal orientation on the sample S. Further advantages will demonstrate the benefits of having the angles $\theta$ and $\psi$ both referenced to a common direction. It should be noted that there can be azimuthal orientations of the sample S (e.g., $\theta_p$) and the transmitting and receiving transducers (e.g., $\psi_r$, $\psi_t$) which are identical, but in general these angles are distinct.

To aid in understanding the present invention, the following discussions and examples are provided. Anisotropic materials can be characterized by the velocity of propagation of orthogonal modes (polarizations) of shear waves in the anisotropic material. In general, given a direction of propagation, there exists two orthogonal modes (polarizations) of shear wave propagation through an anisotropic material. The velocity of propagation of each shear wave mode in such anisotropic materials is different. If the source excitation does not conform to one of the allowed modes, splitting of a shear wave into the two allowed characteristic modes of propagation occurs, and the phenomenon is generally referred to as shear wave birefringence. For a given direction of propagation, there exist two orthogonal shear wave polarizations for the anisotropic materials for which shear wave splitting does not occur and only one of the two allowed shear wave modes (or polarization) propagate. Hereafter, the direction of polarization in anisotropic materials for which a shear wave mode propagates at a velocity greater than the velocity of the other shear wave mode is referred to as the principal elastic axis of the anisotropic material.

Wave propagation through an isotropic material is simple in the sense that only one compressional and one shear wave are expected to propagate along any propagation path. For example, a polarized shear wave propagating from one end of an isotropic sample to the other can be detected by a similarly polarized shear wave transducer and a time series can be recorded using the first embodiment of the test apparatus previously discussed. By keeping the angular orientation $\psi_t$ of the transmitting transducer 20 polarization fixed with respect to the longitudinal axis of the sample S, a plurality of different time series signals can be recorded by imparting shear waves with the transmitting transducer 20 and by rotating the receiving transducer 22 polarization through a plurality of azimuthal orientations $\psi_r$ with respect to the longitudinal axis of the sample S to record the response of the sample S to the imparted shear waves. The orientation of receiving transducer 22 polarization can be changed by rotating azimuthally either clockwise or counterclockwise about the longitudinal axis L of the sample S. As one progresses through azimuthal angles $\psi_r$ (measured from an initial azimuthal orientation in which both the transmitting transducer 20 and the receiving transducer 22 polarizations are aligned at $\psi_r=0°$) event extinction on the recorded time series signal will be observed at an rotation angle of $\psi_r=90°$. Such extinction of an event is predicted when the transmitter and receiver polarization orientations are orthogonal to each other. Similarly, a second event extinction is predicted at a receiver azimuthal angle of $\psi_r=270°$ when the receiving transmitter polarization orientation is again orthogonal to the orientation of the transmitting transducer polarization.

Figure 2:
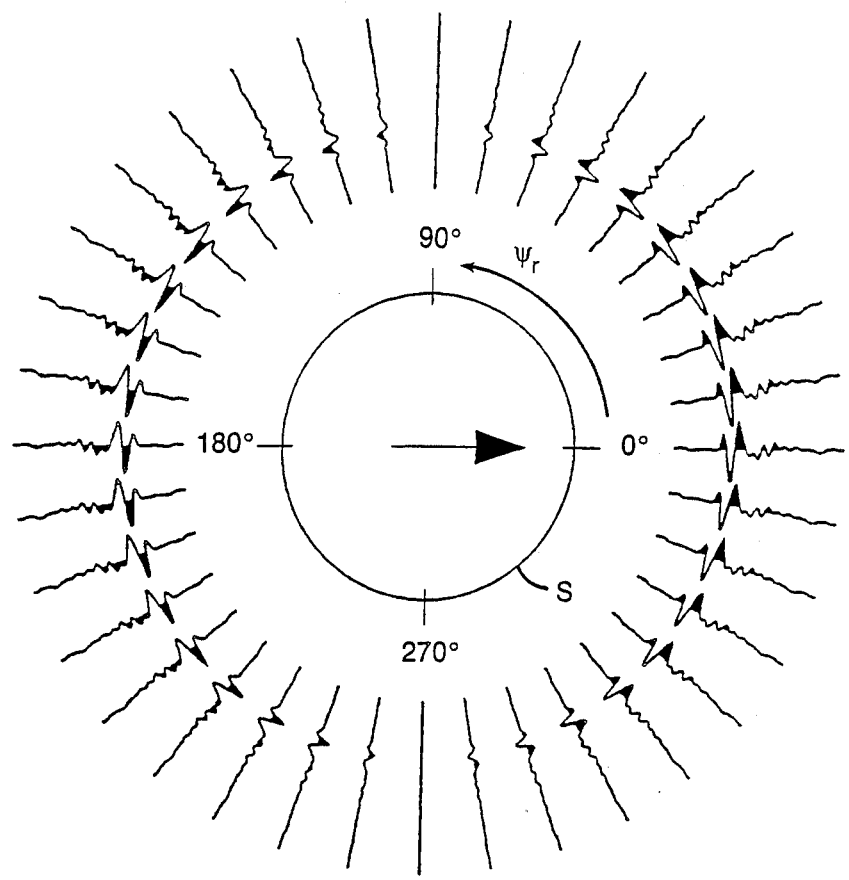
FIG. 2 is a representation of a plurality of time series signals collected for an isotropic material (fused quartz) with a polarized transmitting transducer having a fixed orientation $\psi_t$ and a polarized receiving transducer having a plurality of orientations $\psi_r$.

Looking now to FIG. 2, an experiment was conducted on a sample of isotropic material (e.g., fused quartz) employing the first embodiment of the test apparatus of the present invention. An end view of the sample S is presented with the initial orientation of the transmitting transducer 20 and receiving transducer 22 polarizations indicated with the bold face arrow. As the receiving transducer 22 is rotated counterclockwise through azimuthal angles 104 4 about the longitudinal axis of the sample S, a plurality of time series signals are recorded and displayed at angles $\psi_r$ coincident with the recording thereof. Herein, it is noted that time increases radially outward along each time series signal. Event extinction is clearly evident at azimuthal angles $\psi_r=90°$ and 270°.

Figure 3:
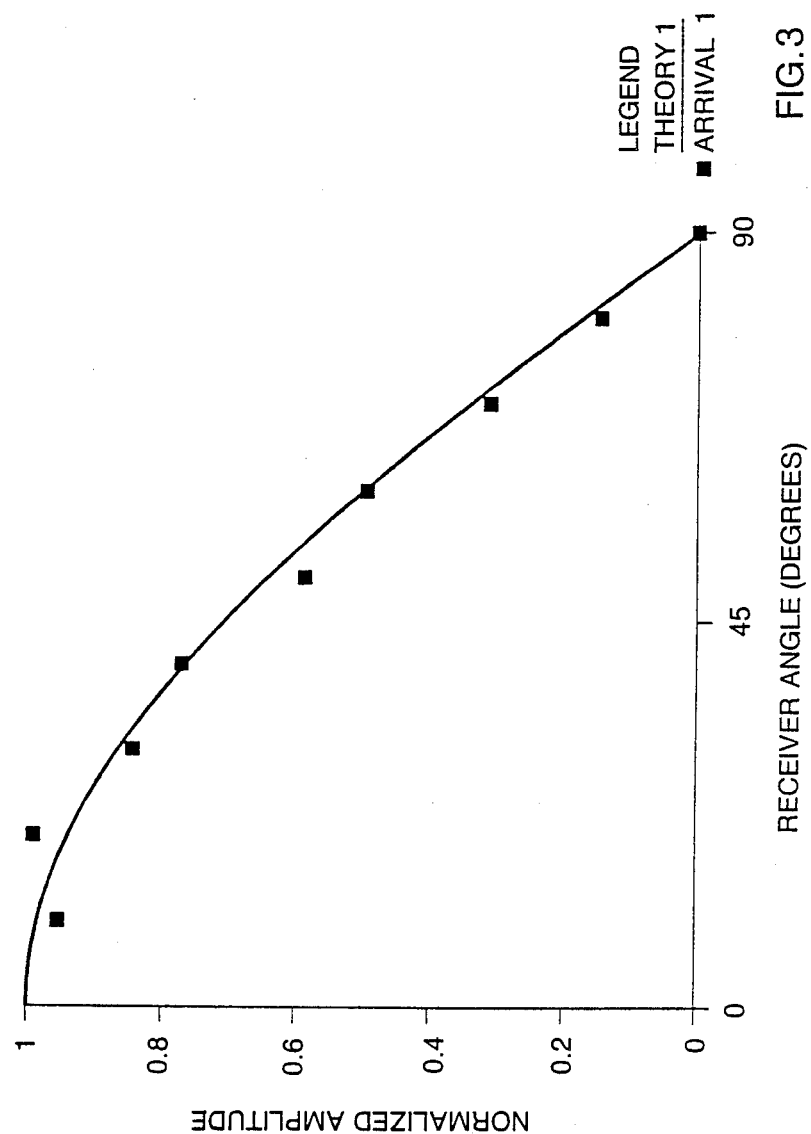
FIG. 3 is a representation of theoretical and observed arrival amplitudes as a function of receiving transducer orientations $\psi_r$.

Simple theoretical considerations predict that the event amplitude should display a simple cosine dependence upon the angle $\psi_r$. In fact, FIG. 3 compares observed event amplitudes (measured at different azimuthal orientations $\psi_r$ of the receiving transducer polarization) to the theoretically predicted amplitudes for the corresponding azimuthal orientation.

Figure 4:
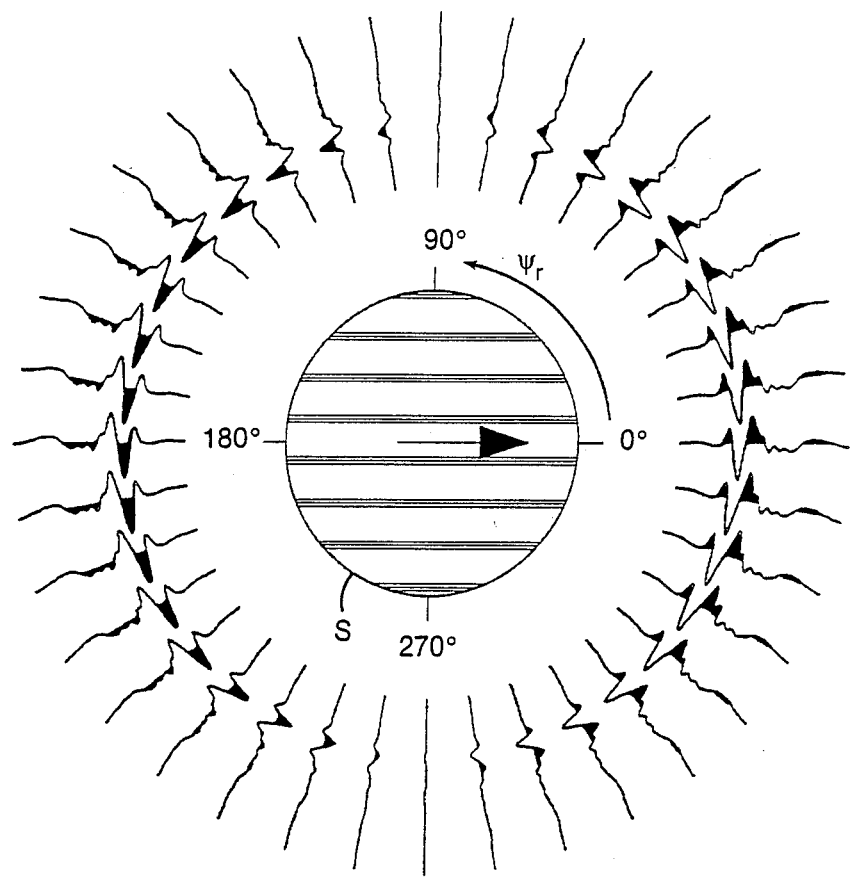
FIG. 4 is a representation of a plurality of time series signals collected for an anisotropic material (McNabb shale) with a polarized transmitting transducer having a fixed orientation $\psi_t$ and a polarized receiving transducer having a plurality of orientations $\psi_r$.

A similar experiment can be performed on anisotropic materials (for example, McNabb Shale). FIG. 4 depicts a plurality of time series signals recorded for the McNabb Shale using the first embodiment of the test apparatus and the measuring technique previously described. The bold face arrow indicates the fixed azimuthal orientation of the polarized transmitting transducer 20 ($\psi_t=0°$) and the initial azimuthal orientation of polarized receiving transducer 22 which are generally aligned with the visual fabric of rock which is indicated by the sets of parallel lines (i.e., $\theta_f=0°$). The time series signals recorded as the receiving transducer 22 is rotated through angles $\psi_r$ about the longitudinal axis of the sample S are shown coincident in azimuth with the location of the recording of such time series signals. The sample S is represented as an end view of a cylinder although those skilled in the art will recognize that other sample shapes can be used. A maximum event amplitude is observed for $\psi_r=0°$, and total event extinction is observed at $\psi_r=90°$ and 270° (i.e., the transmitting transducer 20 and the receiving transducer 22 polarizations are orthogonal). Moreover, only one shear wave event appears to be propagating in the sample S as recorded in the time series signals. A similar experiment can be performed where the polarization of the transmitting transducer 20 is aligned perpendicular to the visual fabric of the sample S. As predicted, one observes only one shear wave event propagating in the sample S; however, it has a slower velocity than that depicted in FIG. 4. Once again, the time series signal has its largest amplitude event when the receiving and transmitting transducer polarizations are parallel, and total extinction of the event in the time series signal is observed at rotation angles $\psi_r$ of 90° and 270° of the receiving transducer 22 measured relative to the orientation of the transmitting transducer 20.

Figure 5:
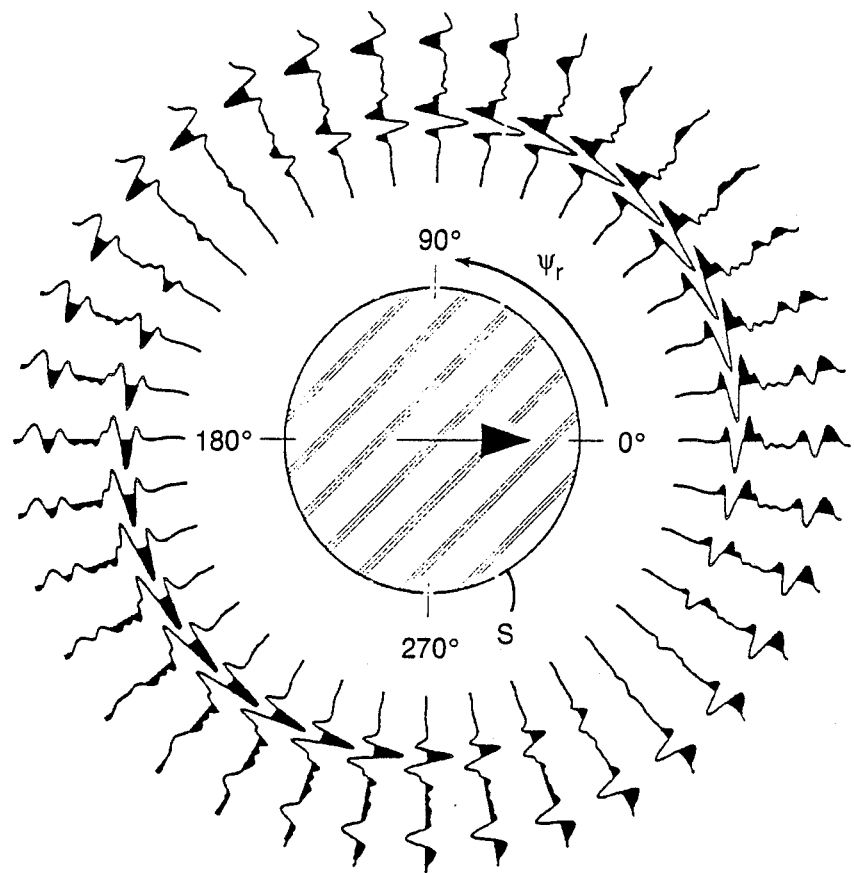
FIG. 5 is a representation of a plurality of time series signals collected for the anisotropic material of FIG. 4; however, the sample has been rotated 45°.

Thus, experiments confirm the theoretical expectations for the existence of distinct shear wave modes propagating at different velocities when the polarization of the transmitting transducer 20 is aligned either parallel or perpendicular to the principal elastic axis of anisotropy of the sample. However, when the principal elastic axis or visual fabric of the sample is not orthogonal with respect to the polarization of the transmitting transducer 20, the recorded time series signals become very complex and confused. FIG. 5 shows a plurality of recorded time series signal as a function of the azimuthal angle $\psi_r$ of the receiving transducer 20 collected using the first embodiment of the test apparatus and method previously discussed. Here, the bold face arrow represents the initial azimuthal orientation of the receiving transducer 22, and the fixed azimuthal orientation $\psi_t$ of the transmitting transducer 20 polarization with respect to the sample S. The parallel lines within the sample S indicate the orientation of the visual fabric of the samples. Here, the visual fabric of the sample S is oriented at an angle $\theta_f=45°$ measured between the visual fabric of sample S and the orientation of the transmitting transducer 20 polarization.

Theoretical expectations for an elastic, anisotropic media assume, for the configuration of FIG. 5, that a shear wave will partition into two orthogonally polarized shear events (modes), one polarized parallel to the elastic fabric and the other perpendicular to it. The amplitude dependence as a function of time for both events can be given by Equation (1).

$$A(t) = S_o \cos\Omega_t \cos\Omega_r f(V_f,t) + S_o \sin\Omega_t \sin\Omega_r f(V_s,t) \quad (1)$$
$$\text{1st event} \qquad\qquad\qquad \text{2nd event}$$

where $S_o$ is the strength of the transmitting transducer 20, $\Omega_t$ and $\Omega_r$ are the respective angles the transmitting and receiving transducer polarizations make with respect to the principal elastic axis of the sample, $f(V_f,t)$ is a wave function at the velocity $V_f$ of the faster propagating mode of the shear wave, and f(V$_s$,t) is a wave function at the velocity Vs of the slower propagating mode of the shear wave. For a fixed transmitting transducer angle $\Omega_t$ and constant applied voltage to the transmitting transducer 20, Equation 1 can be simplified to:

$$A(t) = F_1 \cos\Omega_r + S_1 \sin\Omega_r \qquad (2)$$

S$_1$ and F$_1$ now lump the transmitting transducer source strength S$_0$ and orientation $\Omega_t$ (F$_1$=S$_o$ cos$\Omega_t$ f(V$_f$,t), S$_1$=S$_o$ sin$\Omega_t$ f(V$_s$,t)).

With the receiving transducer 22 polarization aligned parallel to the visual fabric of the sample, one expects that, and indeed observes, a maximum amplitude in the faster traveling shear wave event. Thus, the orientation of the receiving transducer 22 corresponds to $\Omega_r$=0° and hence Equation 2 predicts only one event. Similarly, for the transmitting transducer 20 orientation of $\Omega_t$=0°, Equation 2 predicts one event. At intermediate azimuths $\Omega$ of both the receiving and transmitting transducers, two shear wave events are expected. The distinction and separation of these events depend upon many factors, among which are the magnitude of the velocity anisotropy, the path length, attenuation, source characteristics, etc.

Figure 6:
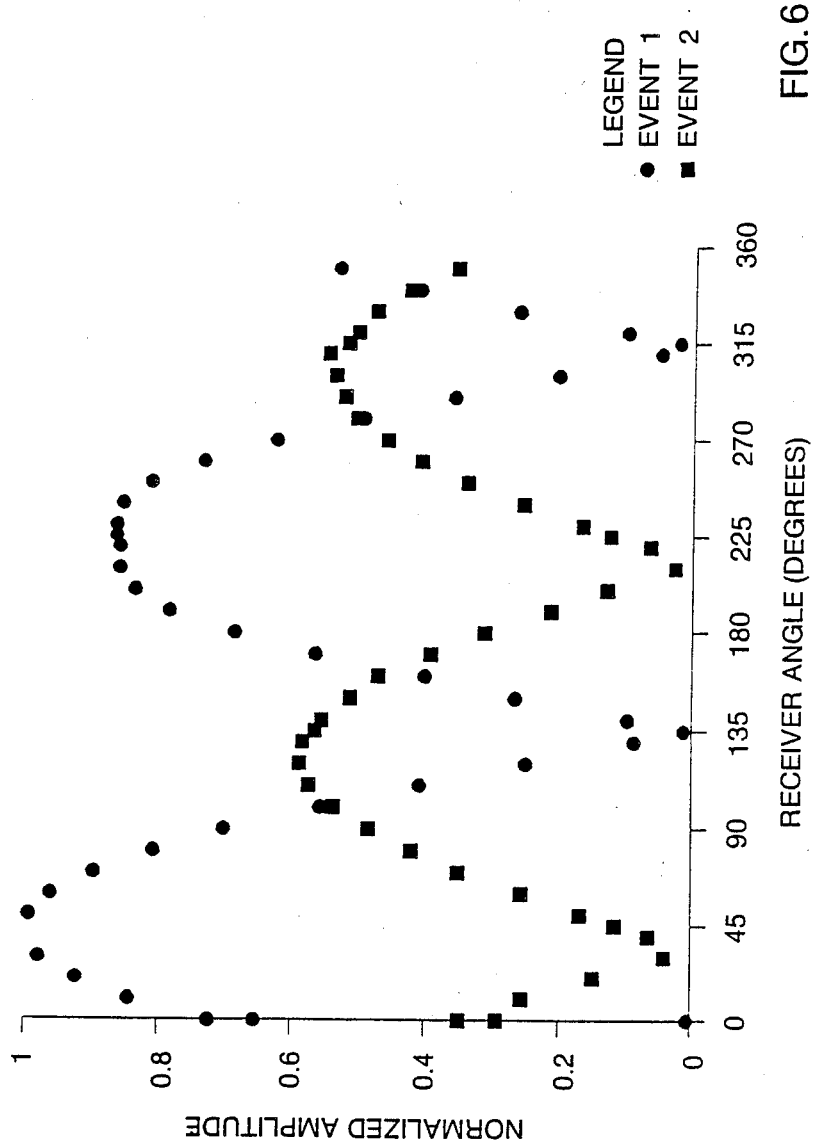
FIG. 6 is a representation of observed amplitudes for both the fast (event 1) and slow (event 2) events of FIG. 5 as a function of the receiver angle $\psi_r$.

McNabb shale samples possess sufficient velocity anisotropy to allow exceptionally clear separation and detection of two shear wave events. Measured amplitudes for the fast and slow events from FIG. 5 are shown in FIG. 6 as a function of the receiving transducer 22 angle $\Omega_r$. This plot shows a trigonometric functional form of the observed amplitudes to be in agreement with the Equation 2 and that the second, slower event exhibits a 90° shift relative to the faster event. There is also a decrease in measured amplitude, most noticeable in the first event with increasing azimuthal angle. Due to the manner in which this experiment was conducted, time increases with each successive observation at increasing azimuthal angles. The degradation of the viscous coupling with time and repeated shearing due to rotation of the receiving transducer 22 with respect to the sample S may be responsible for this amplitude drift. However, at any time or equivalent angle $\Omega_r$, both fast and slow event amplitudes are measured simultaneously so their relative strengths are unaffected. The difference in amplitude at the relative maximum between fast and slow events can be attributed to a number of causes: (1) differences in intrinsic attenuation for the two shear waves; (2) insertion losses due to an acoustic impedance mismatches.

Figure 7:
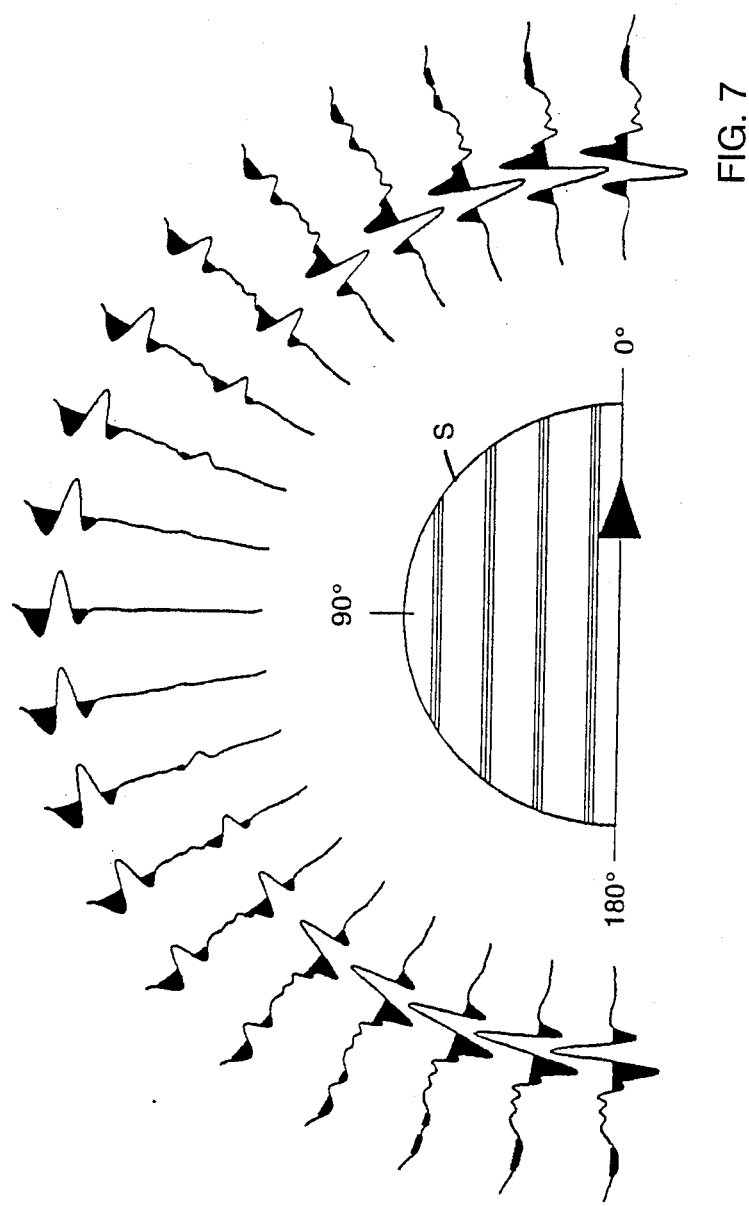
FIG. 7 is a representation of a plurality of time series signals collected for an anisotropic material (McNabb shale) with a polarized transmitting transducer imparting shear waves and a polarized receiving transducer recording time series signals wherein the transmitting and receiving transducer polarizations are rotated simultaneously and synchronously through azimuthal angles of 0–180°.

In the previous experiments, the transmitting transducer 20 polarization was fixed with respect to the visual fabric of the sample. In a subsequent experiment with the McNabb shale sample S using the first embodiment of the test apparatus, the polarization orientations of both the transmitting 20 and receiving 22 transducers were changed simultaneously and synchronously. The recorded time series signals are plotted through 180° of azimuthal angle $\psi$ in FIG. 7. At each azimuthal angle $\psi$, both transmitting 20 and receiving 22 transducer polarizations are aligned and parallel to each other. As expected, two shear wave events are expected giving rise to a fast event at $\psi$=0°. At $\psi$=90° the reverse is true. The maximum amplitude event is the slower of the two events. Notice now that there is no polarity reversal at $\psi$=180° since the phase sensitivity in the transmitting and receiving transducers 20, 22 are preserved during rotation.

Figure 8:
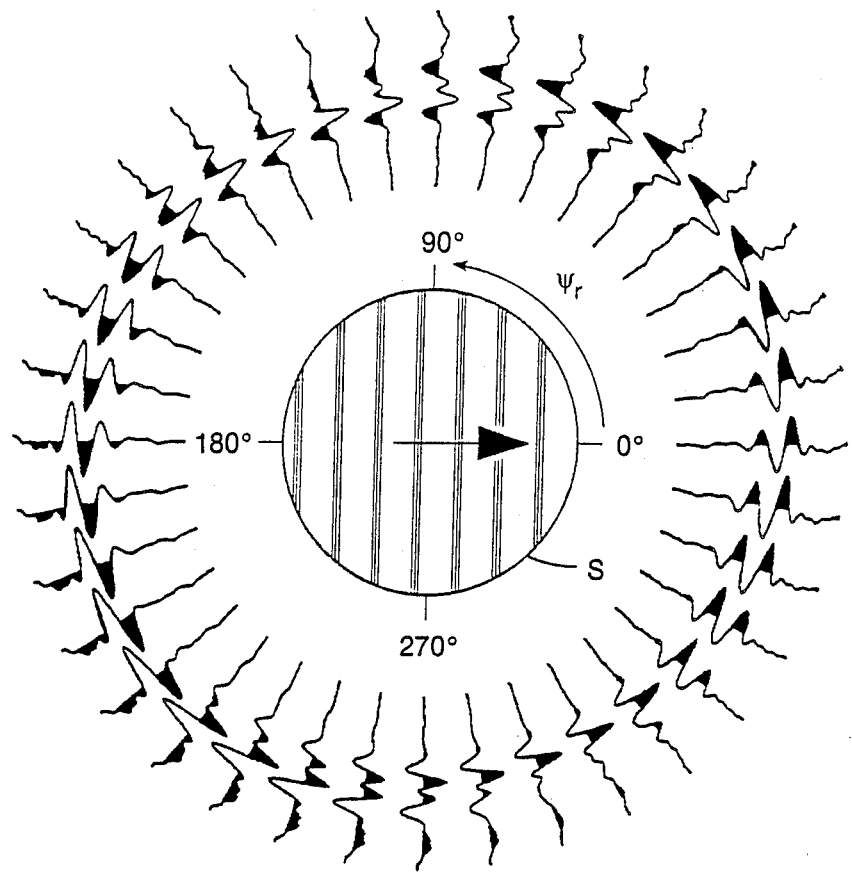
FIG. 8 is a representation of a plurality of time series signals collected for an anisotropic material (Berea sandstone) with a polarized transducer having a fixed orientation $\psi_t$ parallel to the visual bedding planes the anisotropic material and a polarized receiving transmitting transducer having a plurality of orientations $\psi_r$.
Figure 9:
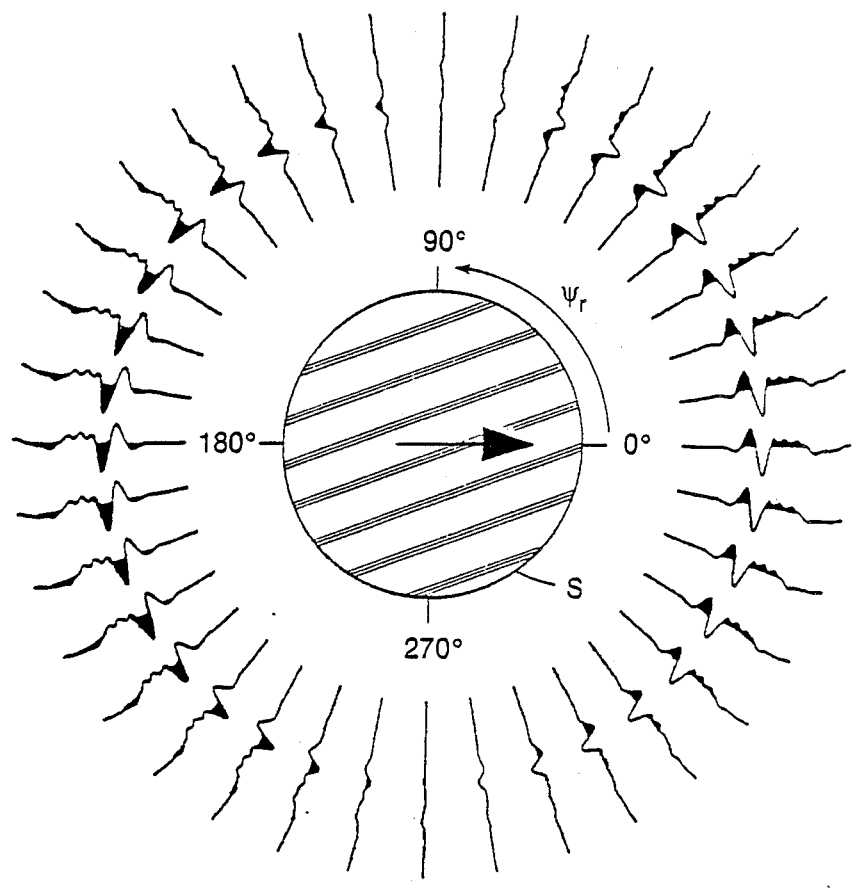
FIG. 9 is a representation of a plurality of time series signals collected for the anisotropic material of FIG. 8 wherein the sample was rotated azimuthally 20° from the position it was in for collecting the time series signals of FIG. 8.

A sample of Berea sandstone was obtained and measured using the first embodiment of the test apparatus and the techniques previously discussed with respect to the McNabb Shale. Time series signals were recorded as a function of receiving transducer 22 polarization azimuth $\psi_r$ as shown in FIG. 8. The transmitting transducer 20 polarization was initially fixed perpendicular to the visual fabric of the sample as indicated by the bold face arrow ensuring that only one slow arrival should be expected. However, the recorded time series signals of FIG. 8 look quite complicated when compared to those recorded on the sample of the McNabb shale anisotropy of Berea sandstone. Examination of the time series signals reveals evidence of two events. However, two shear events were not to be expected when the transmitting transducer polarization was aligned perpendicular to the visual fabric of the samples. In fact, simple, singular events can be noted only at azimuths of $\psi_r$ at approximately 20° and 110°. A physical rotation of the visual fabric of the sample S some 20° to the transmitter polarization yields the time series signal shown in FIG. 9. These time series signals now appear to be as expected for the propagation in a simple anisotropic media. A simple sinusoidal dependency of the event amplitude of a single event and complete extinction when receiving and transmitting transducer polarizations are orthogonal is shown in FIG. 10. Unexpectedly, applicants have found that the Berea sandstone apparently possesses an anisotropy whose principal elastic axis is not aligned with the visual fabric. In fact, principal elastic axis of anisotropy in Berea sandstone is believed to be due to the presence of preferentially aligned microcracks rather than due to aligned minerals as was the case for the McNabb shale samples.

All of the above examples simply confirm expectations which are well understood by those familiar with physics. However, such methods for detecting and measuring elastic anisotropy in formation samples requires recording a plurality of time series signals azimuthally about the longitudinal axis of a sample. Applicant's present invention provides a more expeditious and novel approach to detecting and determining a measure of anisotropy in formation samples. To further motivate this discussion, a simplifying example will first be presented.

Figure 10A:
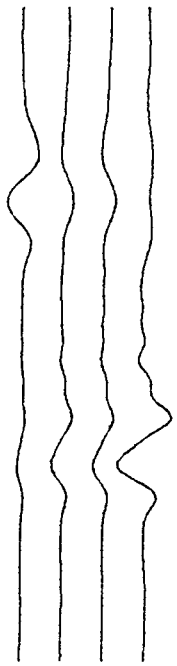
FIG. 10a is a dyad of time series signals $\phi_{ij}$ recorded for an anisotropic material (McNabb shale)
Figure 10B:
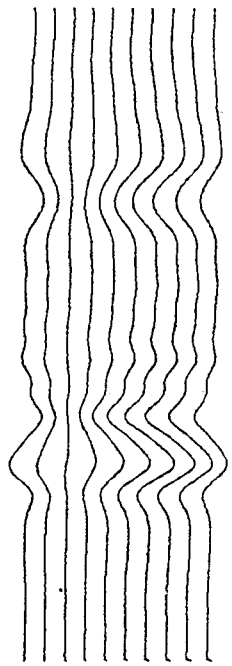
Figure 10C:
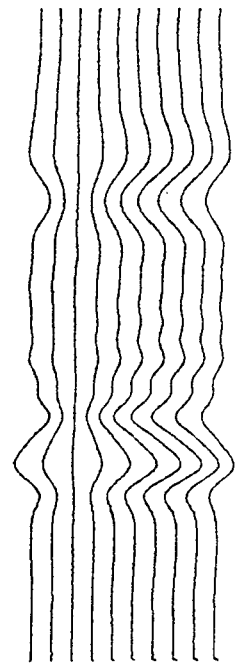

The principal elastic axis of a McNabb shale sample S (similar to that previously evaluated) was oriented at an arbitrary azimuthal angle $\theta_p$ within the first embodiment of the test apparatus. Four time series signals were recorded as shown in FIG. 10a. The first and second time series signals were recorded with receiving transducer 22 first parallel ($\psi_r$=0) and second orthogonal ($\psi_r$=90°) to a first polarization of a first transmitting transducer 20 ($\psi_t$=0°) imparting shear waves into the sample S. Similarly, the third and fourth time series signals were recorded with the receiving transducer 22 first orthogonal ($\psi_r$=90°) and second parallel ($\psi_r$=90°) to a second polarization of the transmitting transducer 22 ($\psi_r$=90°) imparting shear waves into the sample S. It is understood that the azimuthal angles $\psi_t$ and $\psi_r$ are referenced locally and that receiving 22 and transmitting 20 transducer polarizations are at some yet to be determined angles $\Omega$ with respect to the visual fabric or principal elastic axis of the sample. Alternatively, the four recorded time series signals of FIG. 10a could have been obtained with the second embodiment of the test apparatus by imparting shear waves into the sample with a first transmitting transducer having a first polarization ($\psi_t$=0°) and recording the sample's response with first and second receiving transducers having first and second polarizations ($\psi_r=0°$ and $\psi_r=90°$) and by imparting shear waves into the sample with a second transmitting transducer having a second polarization ($\psi_t=90°$) and recording the sample's response with the first and second receiving transducer having first and second polarizations ($\psi_r=0°$ and $\psi_r=90°$).

Applicants have developed a novel method for detecting and measuring the orientation of the principal elastic axis in formation samples using only four recorded time series signals of shear waves transmitted through a sample. To simplify the forthcoming discussion, the recorded time series signals will generally be referred to as a dyad using the notation $\phi_{ij}$. Here, the subscript j indicates the azimuthal orientation $\psi_t$ of the transmitting transducer 20 (i.e., 1=first azimuthal orientation, 2=second azimuthal orientation). Generally, the first and second orientations $\psi_t$ of the transmitting transducer 20 are orthogonal but this is not a necessary condition. Similarly, the subscript i indicates the azimuthal orientation $\psi_r$ of the receiving transducer 22 (i.e., 1=first azimuthal orientation, 2=second azimuthal orientation). Generally, the first and second orientations of the receiving transducer 22 are orthogonal but this is not a necessary condition. Therefore, the first signal in FIG. 10a can be designated $\phi_{11}$; the second, $\phi_{12}$; the third, $\phi_{21}$; and the fourth, $\phi_{22}$. These four time series signals $\phi_{ij}$ are hereafter referred to as a dyad and can be represented as:

$$\phi_{ij} = \begin{matrix} \phi_{11} & \phi_{12} \\ \phi_{21} & \phi_{22} \end{matrix} \quad (3)$$

We have found that by processing the dyad of signals $\phi_{ij}$ the cross component terms of the dyad (i.e., the time series signals $\phi_{12}$ and $\phi_{21}$) can be reduced to substantially zero, thus diagonalizing the dyad of signals. The angle $\Omega$ required to diagonalize the dyad $\phi_{ij}$ can thus be employed to determine the orientation of the principal elastic axis of an anisotropic sample with respect to the azimuthal orientation of the transmitting 20 and receiving 22 transducer polarizations.

Such processing operation can be more simply expressed as:

$$\overline{\phi_{cm}} = C_{ci}(\Omega_r)\phi_{ij}M_{jm}(\Omega_t) \quad (4)$$

where $\overline{\phi_{cm}}$ represents the diagonalized dyad of time series signals, $\phi_{ij}$ represents the recorded time series signals, and $C_{ci}(\Omega_r)$ and $M_{jm}(\Omega_t)$ are rotation operators which can synthetically rotate the orientation of the receiving and transmitting transducer polarizations through an angle $\Omega$.

By trying a series of angles $\Omega_r=\Omega_t=\Omega$ between 0° and 90°, the approximate angle which minimizes the cross component terms of the dyad $\phi_{ij}$ can be determined. In particular, looking to FIGS. 10b and 10c, the cross component terms for the dyad of $\phi_{ij}$ (i.e., $\phi_{12}$ and $\phi_{21}$) are shown after they have been processed for various angles $\Omega$ between 0° and 90° (in 10° increments). It can be seen that the minimum cross-component event amplitudes are obvious, and correspond with the known orientation of the visual fabric and principal elastic axis of the sample with respect to azimuthal orientation of the transmitting transducer (i.e., $\Omega_t=20°$).

By collecting a dyad of time series signals $\phi_{ij}$, as previously discussed, and employing the rotation scheme so as to diagonalize the cross component terms of the dyad, as in Equation (4), the principal elastic axis was determined to be at an azimuth of $\Omega=20°$. In particular, the angles $\Omega_r$ and $\Omega_t$ necessary in Equation (4) to diagonalize the dyad of time series signals $\phi_{ij}$ can be determined as follows:

$$\Omega_r = \frac{\alpha - \gamma}{2} \quad (5a)$$

$$\Omega_t = \frac{\alpha + \gamma}{2} \quad (5b)$$

where $$\alpha = \tan^{-1}\left(\frac{\phi_{12} + \phi_{21}}{\phi_{11} - \phi_{22}}\right) \quad (5c)$$

$$\gamma = \tan^{-1}\left(\frac{\phi_{12} + \phi_{21}}{\phi_{11} - \phi_{22}}\right)$$

where $\Omega_t$ and $\Omega_r$ are respectively the unknown azimuthal orientations of the transmitting transducer 20 and receiving transducer 22 with respect to the principal elastic axis of the sample.

The foregoing discloses a method and apparatus for detecting and measuring elastic anisotropy in formation samples. Those skilled in the art will appreciate that the present method and apparatus can be extended to determine the symmetry of anisotropy in samples of the earth's formations by determining the principal elastic axis in three separate samples taken along mutually orthogonal axes of the earth's formations as well as to extend the method for conditions of elevated temperatures and pressures simulating in-situ formation conditions. It should be further understood that changes can be made to the method and apparatus of the present invention without departing from the scope of the invention as defined in the following claims.

What is claimed:

1. A method for detecting and measuring elastic anisotropy in samples of the earth's formations, comprising the steps of:
   (a) recording a dyad of time series signals representative of the sample's response to imparted shear waves; and
   (b) processing the dyad of time series signals as a group to detect and measure elastic anisotropy in the sample.

2. The method of claim 1 wherein the step of processing the dyad of time series signals includes:
   deagonalizing the dyad of time series signals.

3. The method of claim 1 wherein the step of processing the dyad of time series signals includes:
   (a) rotating the dyad of time series of signals through a plurality of angles; and
   (b) displaying rotated cross component time series signals of the dyad of time series signals for each of the plurality of angles.

4. The method of claim 1 wherein the dyad of time series signals $\phi_{11}$, $\phi_{12}$, $\phi_{21}$ and $\phi_{22}$ are diagonalized according to:

$$\overline{\phi_{cm}} = C_{ci}(\Omega_r)\phi_{ij}M_{jm}(\Omega_t)$$

where $$\phi_{ij} = \begin{matrix} \phi_{11} & \phi_{12} \\ \phi_{21} & \phi_{22} \end{matrix}$$

$C_{ci}(\Omega_t)$ = a first rotation operator
$M_{jm}(\Omega_r)$ = a second rotation operator
$\overline{\phi_{ij}}$ = processed time series signals.

5. The method of claim 4 wherein the angle $\Omega_t$ of the first rotation operator and the angle $\Omega_r$ of the second rotation operator to diagonalize the dyad of time series signals are determined according to:

$$\Omega_r = \frac{\alpha - \gamma}{2}$$

$$\Omega_t = \frac{\alpha + \gamma}{2}$$

where $$\alpha = \tan^{-1}\left\{ \frac{\phi_{12} + \phi_{21}}{\phi_{11} - \phi_{22}} \right\}$$

$$\gamma = \tan^{-1}\left\{ \frac{\phi_{12} + \phi_{21}}{\phi_{11} + \phi_{22}} \right\}$$

6. The method of claim 5 wherein
(a) angle $\Omega_t$ provides an angular measure of the azimuthal relationship of the polarization of the transducer imparting shear waves into the sample measured from a principal axis of the sample; and
(b) the angle $\Omega_r$ provides an angular measure of the azimuthal relationship of the polarizations of the first and second receiver measured from the principal axis of the sample.

7. An apparatus for detecting and measuring elastic anisotropy in samples of the earth's formations, comprising:
(a) shear wave transducer means for recording a dyad of time series signals representative of a sample's response to imparted shear waves; and
(b) processing means for processing the dyad of time series signals as a group to detect and measure elastic anisotropy in the sample of the earth's formations.

8. The apparatus of claim 7, wherein the shear wave transducer means includes:
(a) shear wave transmitting transducer means for imparting first and second distinctly polarized shear waves into the sample; and
(b) shear wave receiving transducer means for recording first and second time series signals of each of the first and second distinctly polarized shear waves imparted into the sample.

9. The apparatus in claim 8 wherein:
(a) the shear wave transmitting transducer means comprises first and second shear wave transmitting transducers having orthogonal polarizations; and
(b) the shear wave receiving transducer means comprises first and second receiving transducer having orthogonal polarizations.

10. The apparatus of claim 9 wherein the polarizations of the first and second transmitting transducers match the polarizations of the first and second receiving transducers.

11. The apparatus of claim 8 wherein:
(a) the shear wave transmitting transducer means comprises a shear wave transmitting transducer rotatable between first and second polarizations; and
(b) the shear wave receiving transducer means comprises a shear wave receiving transducer rotatable between first and second polarizations.

12. A method for detecting and measuring elastic anisotropy in samples of material, comprising the steps of:
(a) imparting a first shear wave into the sample with a transducer having a first polarization;
(b) recording first and second time series signals $\phi_{11}$, $\phi_{21}$ representative of the sample's response to the imparted first shear wave with a set of receivers having first and second polarization;
(c) imparting a second shear wave into the sample with a transducer having a second polarization;
(d) recording first and second time series signals $\phi_{12}$, $\phi_{22}$ representative of the sample's response of the imparted second shear wave with the second set of receivers having first and second polarizations, wherein the time series signals $\phi_{11}$, $\phi_{12}$, $\phi_{21}$, and $\phi_{22}$ comprise a dyad of time series signals; and
(e) processing the dyad of time series signals as a group to determine the azimuthal orientation of the principle elastic axis of the sample.

13. The method of claim 12 wherein the step of processing the dyad of time series signals includes:
diagonalizing the dyad of time series signals so as to minimize the amplitude of selected events in the signals $\phi_{12}$ and $\phi_{21}$, and to maximize the amplitude of selected events in the signals $\phi_{11}$ and $\phi_{22}$.

14. The method of claim 13 wherein the dyad of time series signals $\phi_{11}$, $\phi_{12}$, $\phi_{21}$ and $\phi_{22}$ are diagonalized according to:

$$\overline{\phi_{cm}} = C_{ci}(\Omega_r)\phi_{ij}M_{jm}(\Omega_t)$$

where $$\phi_{ij} = \begin{matrix} \phi_{11} & \phi_{12} \\ \phi_{21} & \phi_{22} \end{matrix}$$

$C_{ci}(\Omega_r)$ = a first rotation operator,
$M_{jm}(\Omega_t)$ = a second rotation operator, and
$\overline{\phi_{cm}}$ = processed time series signals.

15. The method of claim 12 wherein the step of processing the dyad of time series signals includes:
(a) rotating the dyad of time series signals through a plurality of angles so as to minimize the amplitude of selected events in the signals $\phi_{12}$ and $\phi_{21}$, and to maximize the amplitude of selected events in the signals $\phi_{11}$ and $\phi_{22}$; and
(b) obtaining a measure of the velocity of the shear wave propagation in a sample associated with each of the selected events in the signals $\phi_{11}$ and $\phi_{22}$ which have been maximized.

16. An apparatus for detecting and measuring elastic anisotropy in samples of material under in-situ conditions of temperature and pressure, comprising:
(a) shear wave transmitting transducer means for imparting first and second distinctly polarized shear waves into the sample;
(b) shear wave receiving transducer means for recording first and second time series signals of each of the first and second distinctly polarized shear waves imparted into the sample where the recorded time series signals comprise a dyad of time series signals; and (c) processing means for processing the dyad of time series signals as a group to determine the azimuthal orientation of the principal elastic axis of the sample under in-situ conditions wherein such in-situ conditions can include temperature and pressure.

17. The apparatus in claim 16 wherein:
(a) the shear wave transducer means comprising first and second shear wave transmitting transducers having different polarizations; and
the shear wave receiving transducer means comprising first and second receiving transducers having different polarizations.

18. The apparatus of claim 16 wherein:
(a) the shear wave transmitting transducer means comprise a shear wave transmitting transducer rotatable between first and second polarizations; and
(b) shear wave receiving transducer means comprise a shear wave receiving transducer rotatable between first and second polarizations.

19. A method for detecting and measuring elastic anisotropy in samples of a material, comprising the steps of:
(a) imparting a first shear polarization; sample with a transducer having a first polarization;
(b) recording first and second time series signals $\phi_{11}, \phi_{21}$ representative of the sample's response to the imparted first shear wave with a set of receivers having first and second polarizations;
(c) imparting a second shear wave into the sample with a transducer having a second polarization;
(d) recording first and second time series signals $\phi_{12}, \phi_{22}$ representative of the sample's response to the imparted second shear wave with the set of receivers having first and second polarizations, wherein the time series signals $\phi_{11}, \phi_{12}, \phi_{21},$ and $\phi_{22}$ comprise a dyad of time series signals; and
(e) diagonalizing the dyad of time series signals so as to minimize the amplitude of selected events in the signals $\phi_{12}$ and $\phi_{21}$ and to maximize the amplitude of selected events in the signals $\phi_{11}$ and $\phi_{22}$.

20. The method of claim 19 further including:
obtaining a measure of the velocity of shear wave propagation in the sample associated with each of the selected events in the signals $\phi_{11}$ and $\phi_{22}$ which have been 21. The method of claim 19 wherein the dyad of time series signals $\phi_{11}, \phi_{12}, \phi_{21}$ and $\phi_{22}$ are diagonalized according to:

$$\overline{\phi_{cm}} = C_{ci}(\Omega_r)\phi_{ij}M_{jm}(\Omega_t)$$

where $$\phi_{ij} = \begin{matrix} \phi_{11} & \phi_{12} \\ \phi_{21} & \phi_{22} \end{matrix}$$

$C_{ci}(\Omega_t)$ = a first rotation operator
$M_{jm}(\Omega_r)$ = a second rotation operator
$\overline{\phi}_{ij}$ = processed time series signals.

22. The method of claim 21 wherein the angle $\Omega_t$ of the first rotation operator and the angle $\Omega_r$ of the second rotation operator to diagonalize the dyad of time series signals are determined according to:

$$\Omega_r = \frac{\alpha - \gamma}{2}$$

$$\Omega_t = \frac{\alpha + \gamma}{2}$$

where $$\alpha = \tan^{-1}\left(\frac{\phi_{12} + \phi_{21}}{\phi_{11} - \phi_{22}}\right)$$

$$\gamma = \tan^{-1}\left(\frac{\phi_{12} + \phi_{21}}{\phi_{11} + \phi_{22}}\right)$$

23. The method of claim 22 wherein:
(a) angle $\Omega_t$ provides an angular measure of the azimuthal relationship of the polarization of the transducer imparting shear waves into the sample measured from a principal axis of the sample; and
(b) the angle $\Omega_r$ provides an angular measure of the azimuthal relationship of the polarizations of the first and second receiver measured from the principal axis of the sample.

24. An apparatus for detecting and measuring elastic anisotropy in samples of a material under in-situ conditions of temperature and pressure, comprising:
(a) shear wave transmitting transducer means for imparting first and second distinctly polarized shear waves into the sample;
(b) shear wave receiving transducer means for recording first and second time series signals of each of the first and second distinctly polarized shear waves imparted into the sample, wherein the recorded time series signals comprise a dyad of time series signals; and
(c) processing means for diagonalizing the dyad of time series signals as a group to determine the azimuthal orientation of the principal elastic axis of the sample under in-situ conditions, wherein such in-situ conditions can include temperature and pressure.

25. The apparatus of claim 24 wherein:
(a) the first and second distinctly polarized shear waves imparted into the sample have orthogonal polarizations; and
(b) the first and second time series signals recorded of each of the first and second distinctly polarized shear waves imparted into the sample have orthogonal polarizations.

26. The apparatus of claim 24 wherein:
(a) the shear wave transmitting transducer means comprises first and second shear wave transmitting transducers having different polarizations; and
(b) the shear wave receiving transducer means comprises first and second receiving transducers having different polarizations.

27. The apparatus of claim 26 wherein the polarizations of the first and second transmitting transducers match the polarizations of the first and second receiving transducers.

28. The apparatus of claim 24 wherein:
(a) the shear wave transmitting transducer means comprises a shear wave transmitting transducer rotatable between first and second polarizations; and (b) the shear wave receiving transducer means comprises a shear wave receiving transducer rotatable between first and second polarizations.

29. A method for determining the azimuthal orientation of the principal elastic axis of an anisotropic sample of material, comprising the steps of:
 (a) recording a dyad of time series signals $\phi_{ij}$ representative of the sample's response to shear waves imparted therein with transmitters having polarizations i and recorded by receivers having polarizations j;
 (b) processing the dyad of time series signals $\phi_{ij}$ so as to determine azimuthal angles which maximize the amplitude of events in selected of the dyad of time series signals $\phi_{ij}$;
 (c) determining velocities of propagation of the shear waves associated with the events for which the amplitudes have been maximized; and
 (d) locating the azimuthal orientation of the sample with the azimuthal angle associated with the maximum determined shear wave velocity.

* * * * *

UNITED STATES PATENT AND TRADEMARK OFFICE
CERTIFICATE OF CORRECTION

PATENT NO. : 4,912,979

DATED : April 3, 1990

INVENTOR(S) : C. H. SONDERGELD, ET AL

It is certified that error appears in the above--identified patent and that said Letters Patent is hereby corrected as shown below:

Column 3, line 4, "planes the" should read --planes of the--.

Column 5, line 46, "$104_4$" should read -- $\Psi_r$ --.

Column 10, lines 18-20, (equation) should read $$-- \gamma = \tan^{-1}\left\{\frac{\Phi_{12} - \Phi_{21}}{\Phi_{11} + \Phi_{22}}\right\} --.$$

Claim 5, (last equation) should read $$-- \gamma = \tan^{-1}\left\{\frac{\Phi_{12} - \Phi_{21}}{\Phi_{11} + \Phi_{22}}\right\} --.$$

Claim 19, line 4, "shear polarization; sample" should read --shear wave into the sample--.

Claim 20, line 5, after "have been" insert --maximized--.

Claim 22, (second equation) should read $$-- \Omega t = \frac{\alpha - \gamma}{2} --.$$

UNITED STATES PATENT AND TRADEMARK OFFICE
CERTIFICATE OF CORRECTION

PATENT NO. : 4,912,979

DATED : April 3, 1990

INVENTOR(S) : C. H. SONDERGELD, ET AL

It is certified that error appears in the above-identified patent and that said Letters Patent is hereby corrected as shown below:

Claim 22, (last equation) should read $$-- \gamma = \tan^{-1}\left\{\frac{\Phi_{12} - \Phi_{21}}{\Phi_{11} + \Phi_{22}}\right\} --.$$

Signed and Sealed this

Seventh Day of April, 1992

Attest:

HARRY F. MANBECK, JR.

*Attesting Officer*  *Commissioner of Patents and Trademarks*